US012583833B2

(12) United States Patent
Eh et al.

(10) Patent No.: US 12,583,833 B2
(45) Date of Patent: Mar. 24, 2026

(54) ENRICHMENT OF A DIASTEREOMER IN MAGNOLAN

(71) Applicant: Symrise AG, Holzminden (DE)

(72) Inventors: Marcus Eh, Holzminden (DE); Susanne Borchert, Holzminden (DE); Marcus Betzer, Holzminden (DE); Alexandre Illan, Holzminden (DE); Johannes Heppekausen, Holzminden (DE)

(73) Assignee: Symrise AG, Holzminden (DE)

( * ) Notice: Subject to any disclaimer, the term of this patent is extended or adjusted under 35 U.S.C. 154(b) by 547 days.

(21) Appl. No.: 18/019,782

(22) PCT Filed: Aug. 12, 2021

(86) PCT No.: PCT/EP2021/072541

§ 371 (c)(1),
(2) Date: Feb. 3, 2023

(87) PCT Pub. No.: WO2022/043089

PCT Pub. Date: Mar. 3, 2022

(65) Prior Publication Data

US 2023/0286937 A1 Sep. 14, 2023

(51) Int. Cl.

*C07D 319/08* (2006.01)
*C11B 9/00* (2006.01)

(52) U.S. Cl.

CPC ............ *C07D 319/08* (2013.01); *C11B 9/008* (2013.01)

(58) Field of Classification Search

CPC .............................. C07D 319/08; C11B 9/008
USPC .................................................. 512/14, 8, 1
See application file for complete search history.

(56) References Cited

FOREIGN PATENT DOCUMENTS

| | | | | |
|---|---|---|---|---|
| DE | 1793310 A1 | 2/1972 | | |
| EP | 0982303 A1 | 1/2000 | | |
| WO | 2010142815 A2 | 12/2010 | | |
| WO | WO-2022042829 A1 * | 3/2022 | ............. | C11B 9/008 |

OTHER PUBLICATIONS

Abate et al, Enzyme-Mediated Preparation of Chiral 1,3-Dioxane Odorants, 2003, Helvetica Chimca Acta, vol. 86, 592-606 (Year: 2003).*

Eh et al, WO 2022042829 Machine Translation, Mar. 3, 2022 (Year: 2022).*

Elke Fritz-Langhals, 1993, "Separation of Diastereomers by Distillation—A New Procedure for the Synthesis of Optically Active Herocyclic Carboxylic Acids" Angew. Chem. Int. Ed. Engl, vol. 32 (5), pp. 753-754.

Eliel, et al., 1994, "General Methods for the Separation of Diastereomers" pp. 374-381.

Bruns, et al., 1979, "Stereochemistry of Cyclic Compounds—I, Synthesis and Configurational Assignment of Diastereomeric 2,4-Dioxaspiro{5.5}Undec-8-Enes", Tetrahedron, Elsevier Science Publishers, vol. 35, pp. 2523-2530.

Abate, et al., 2003, "Enzyme-Mediated Preparation of Chiral 1,3-Diaxane Odorants", Helvetica Chimica Acta, vol. 86, pp. 592-606.

* cited by examiner

*Primary Examiner* — Jessica Whiteley
(74) *Attorney, Agent, or Firm* — McDonnell Boehnen Hulbert & Berghoff LLP

(57) ABSTRACT

The invention relates to a distillative process for the preparation of a diastereomer-enriched odorant mixture, and to the diastereomer-enriched odorant mixture and its use as an odorant or for the preparation of an odorant composition. Furthermore, the invention relates to the use of the diastereomer-enriched odorant mixture for imparting, modifying or enhancing a floral odour note of a perfumed product or for the preparation of a perfumed product. Finally, the present invention also relates to odorant compositions and perfumed products comprising the diastereomer-enriched odorant composition.

20 Claims, 4 Drawing Sheets

ENRICHMENT OF A DIASTEREOMER IN MAGNOLAN

CROSS-REFERENCE TO RELATED APPLICATIONS

This application is the US national phase under 35 U.S.C. § 371 of International Application No. PCT/EP2021/072541, filed Aug. 12, 2021, which claims priority to International Application No. PCT/EP2020/073775, filed Aug. 25, 2020, the contents of each of which are hereby incorporated by reference in their entirety.

FIELD OF THE INVENTION

The invention relates to a distillative process for the preparation of a diastereomer-enriched odorant mixture with a floral note comprising compounds of the general formula (A):

Formula (A)

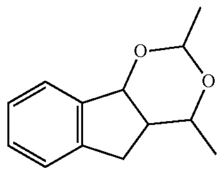

as well as the diastereomer-enriched odorant mixture comprising compounds of the general formula (A) preparable from this process and its use as a odorant or for the preparation of a odorant composition. Furthermore, the invention relates to the use of the diastereomer-enriched odorant mixture for imparting, modifying or enhancing a floral odour note of a perfumed product or for the preparation of a perfumed product itself. Ultimately, the present invention relates to odorant compositions and perfumed products comprising the diastereomer-enriched odorant blend.

STATE OF THE ART 4,4a,5,9b-Tetrahydro-2,4-dimethylindeno[1,2-d][1,3]dioxin is a popular fragrance or odorant, which primarily has a transparent, floral-green odour and is reminiscent of the scent of magnolias, geraniums and grapefruit. Often, the smell of this compound is also described as flowery-green and very complex. This is why Magnolan (Symrise AG), as this odorant is commercially known, is used in particular to create floral fragrances.

Furthermore, Magnolan (Symrise AG) is excellently suited for achieving specific floral notes in floral compositions and for achieving a special olfactory effect in olfactory compositions comprising dry and woody components.

The disclosure document DE 1 793 310 describes 2,6-dialkyl-4,5-indano-1,3-dioxane compounds, a process for the preparation of these compounds and the use of these compounds in perfume production and in perfumery products as a perfume base. Also disclosed therein is the preparation of 2,6-dimethyl-4,5-(1',2'-indeno)-1,3-dioxane, which has a rose-like odour similar to Damascene rose. In this regard, the product produced has two geometric isomers which are present in a ratio of 1.8:1. In particular, the fragrance in question is intended to be used to supplement or replace natural rose fragrances.

WO 2010/142815 A2 also discloses a fragrance mixture comprising magnolan. The olfactory properties of the fragrance are described as "white flower (especially white *magnolia*), floral (red flower, peony, geranium) and "indolic".

Although the already established fragrance Magnolan (Symrise AG) basically has excellent olfactory properties, it is however often described that this fragrance also has a rather disturbing, technical and plastic-like odour.

As described in DE 1 793 310, this is usually a product in which the mutually diastereomeric isomers are present next to each other in almost equal distribution.

TASK OF THE INVENTION

Accordingly, the invention is primarily based on the general task of optimising the commercially available odorant and eliminating the disturbing odour notes and thus ensuring an intensive, more harmonious and "cleaner" floral odour impression and providing a corresponding process for producing such an optimised odorant.

A gentle process is of utmost importance in order to minimise any decomposition processes and potential side reactions as well as interactions between such decomposition products or side reaction products, which could further adversely affect the olfactory properties of the product itself or the fragrance preparations and perfumed products containing the rich substance.

Although methods are already known to produce magnolan, these processes usually show disadvantages in isomer purity, especially when upscaling, i.e. producing the product on a large (industrial) scale: often only low yields and selectivities, i.e. low purity, can be observed. This consequently has a detrimental effect on the quality of the product, and especially on the odour properties as explained before.

Thus, a further object of the present invention is to provide a simple and gentle manufacturing process which enables an optimised floral fragrance to be produced in a few steps and thus to provide the desired products simultaneously at low cost and in high yield and purity.

Furthermore, a task relates to the provision of such a odorant mixture, its use as a odorant and for the production of odorant preparations and perfumed products as well as odorant preparations and perfumed products comprising this optimised odorant mixture.

An additional task of the invention relates to the reduction or masking of an unpleasant odour and/or the enhancement of positive odour impressions, in particular the enhancement of harmonious, intense and "clean" floral odour impressions.

A further task concerns the gentle enrichment of isomers of positive odour properties and thus the targeted influencing of the odour without damaging the odiferous substances or changing their odour.

The synthesis is conceivable, for example, starting from the use of optically active starting materials, i.e. starting materials in which the stereoselectivity of the starting compounds determines the stereoisomerism of the products, or from isolated diastereomers. However, such a process is associated with a large number of complex and time-consuming preceding synthesis and purification steps to provide the isolated enantiomers or diastereomers of the starting compounds. In this respect, a further task of the present invention also arises, namely the provision of diastereomer-enriched magnolan products without the need to provide isomer-directing intermediates as starting or intermediate steps, or to provide a fast and efficient process with few process steps, which at the same time ensures a high selectivity and also largely prevents decomposition reactions or side reactions, which could otherwise have a detrimental effect on the odour properties.

The tasks posed are solved according to the invention by the objects of the independent patent claims. Further aspects and preferred embodiments of the present invention result from the wording of the dependent patent claims, the following description and the embodiment examples.

SUMMARY OF THE INVENTION

A first aspect of the present invention relates to a distillative process for the preparation of a diastereomer-enriched odorant mixture with a floral note comprising compounds of the general formula (A):

Formula (A)

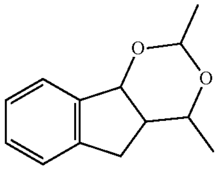
, wherein the odorant mixture comprises the following diastereomeric pairs of enantiomers:

Enantiomeric pair (I):

Formula (Ia)

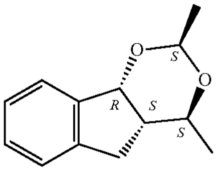

Formula (Ib)

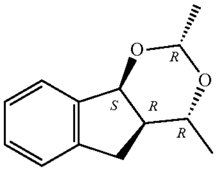

Enantiomeric pair (II):

Formula (IIa)

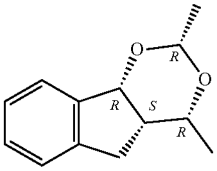

Formula (IIb)

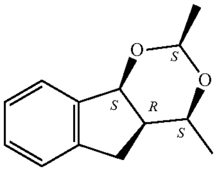

Enantiomeric pair (III):

-continued

Formula (IIIa)

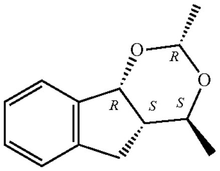

Formula (IIIb)

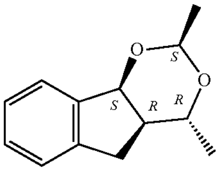

wherein the ratio of the enantiomeric pair (I) and the enantiomeric pair (II) to each other is at least 10:1 and the ratio of the enantiomeric pairs (I) and (III) to each other is at least 50:1, and wherein the process comprises the following distillative steps:

(a) separation by distillation of a crude product comprising compounds of the general formula (A) in a first distillation step;

(b) subsequent fine distillation of the crude product over one or more distillation steps to concentrate the enantiomeric pair (I) relative to the enantiomeric pairs (II) and (III), wherein the fine distillation comprises at least 15 separation steps.

It has been shown that fragrance blends with lower amounts of isomer (III) have a better olfactory impression of the Magnolan odorant. Furthermore, the fragrance blends should contain higher amounts of isomer (I) in relation to isomer (II). This selective enrichment is surprising, as no selective enrichment of the enantiomer pair (I) relative to the enantiomer pairs (II) or (III) was previously known, nor is it to be expected. In particular, such high enrichments are surprising. Furthermore, this enrichment was achieved with procedurally advantageous processes that are both cost-effective and efficient.

In a second aspect, the present invention comprises a diastereomerically enriched odorant mixture comprising compounds of the general formula (A), wherein the compounds of formula (A) comprise the mutually diastereomeric enantiomer pairs of formulae (I), (II) and (III) and wherein the quantity ratio of the enantiomer pair (I) and the enantiomer pair (II) to each other is at least 10:1 and the ratio of the enantiomeric pairs (I) and (III) to one another is at least 50:1 (based on the total odorant mixture comprising compounds of the general formula (A), i.e. compounds (I), (II) and (III)).

The third aspect of the present invention is the use of the diastereomer-enriched odorant mixture as an odorant or for the preparation of a odorant composition.

In a fourth aspect, the present invention relates to a fragrance composition comprising a sensory effective amount of the diastereomer-enriched fragrance mixture.

Another aspect of the present invention is the use of the diastereomer-enriched odorant mixture in a sensory effective amount for imparting, modifying or enhancing a floral odour note of a perfumed product or for the preparation of a perfumed product as such.

Finally, in another aspect, the present invention relates to a perfumed product comprising the diastereomer-enriched odorant composition or an odorant composition comprising the same.

Surprisingly, it has been found in the context of the present invention that by means of the process described herein (preferably racemic) diastereomer-enriched fragrance blends can be obtained which exhibit a more natural and intense floral, rosy, warmer, transparent and radiant geranium-scented odour profile which is perceived as less technical and does not exhibit odour notes reminiscent of plastic compared to commercially available magnolan. In addition, compared to commercially available Magnolan, the smell is perceived as less green, more intensely rosy and less reminiscent of grapefruit.

Furthermore, with the process described herein, it is possible to provide the (preferably racemic) diastereomer-enriched odorant mixture in very high yield and excellent purity in only a few synthesis and process steps, which distinguish the process described herein as a highly efficient, highly selective and reliable, i.e. reproducible, process. The resulting odorant with an intense floral note enable the production of improved fragrance compositions with particular olfactory notes and aspects without the irritating technical and plastic-smelling odour components. Accordingly, the odour of the substances, preparations and products described herein is perceived as more floral and "cleaner".

These and other aspects, as well as other features and advantages of the present invention, will be apparent to those skilled in the art from a study of the following detailed description and claims. In this regard, any feature from one aspect of the invention may be used or substituted in another aspect of the invention. The examples contained in the present application describe the invention without limiting it.

Advantageous further embodiments and variants of the invention are given in the dependent claims.

All percentages are by weight unless otherwise stated. Numerical examples given in the form "from x to y" include the values given. When multiple preferred numerical ranges are given in this format, all ranges resulting from the combination of the different endpoints are also included.

FIGURES

FIGS. 1*a* and 1*b* show the $^{1}$H-NMR spectrum (600 MHz, chloroform-d) of a first diastereomer-enriched odorant mixture according to the invention.

DETAILED DESCRIPTION OF THE INVENTION

Figure 1A:
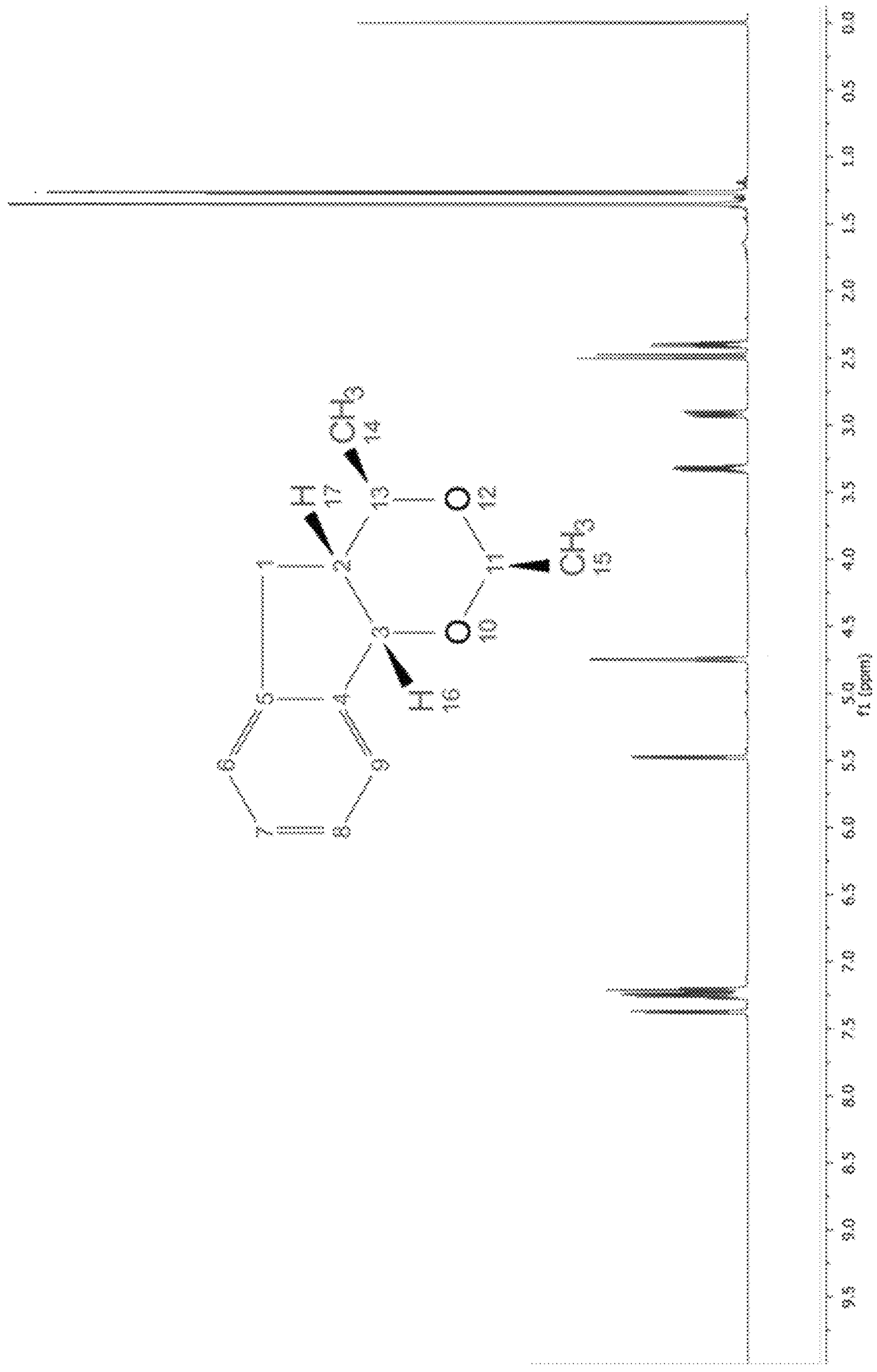
Figure 1B:
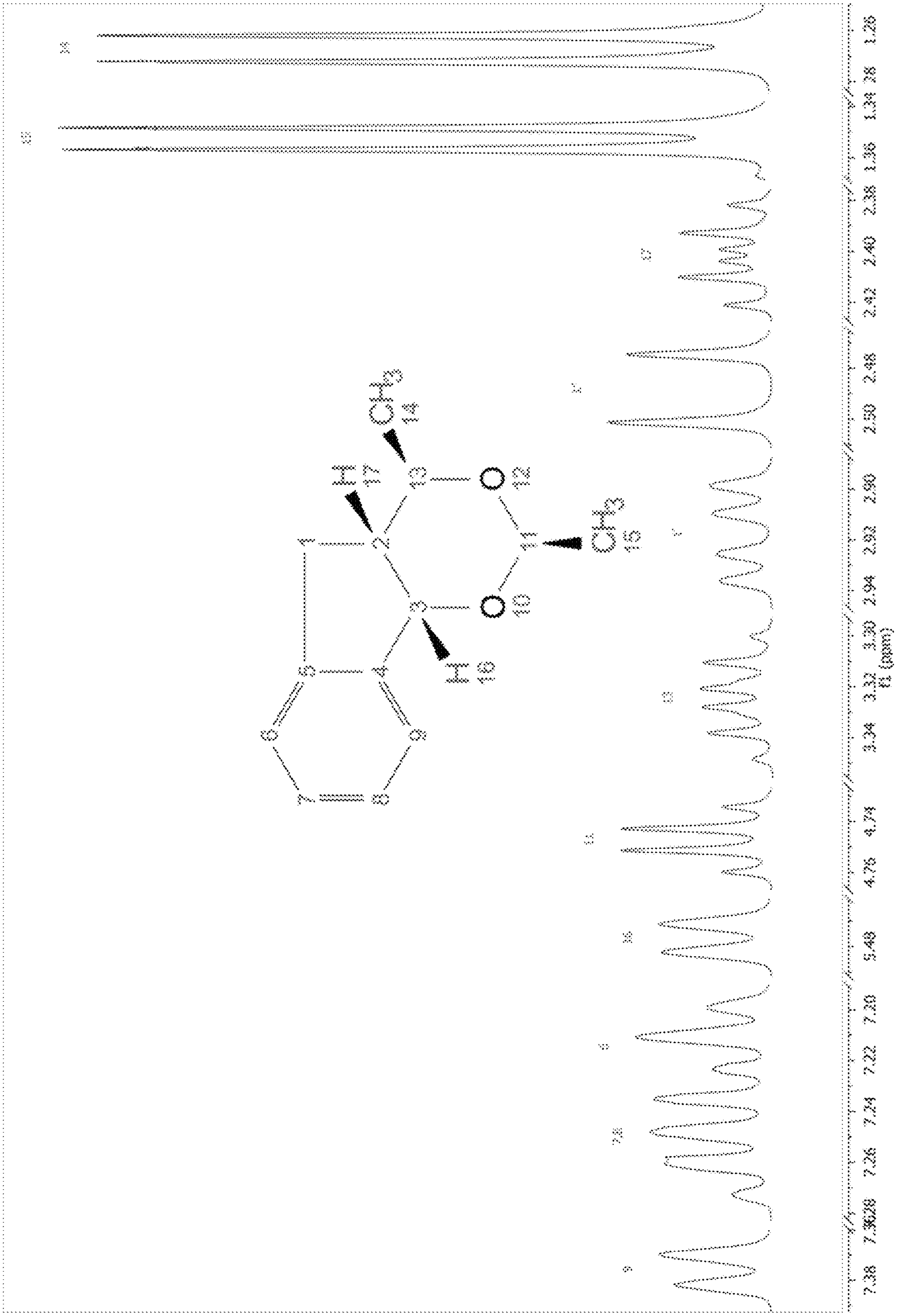
Figure 2:
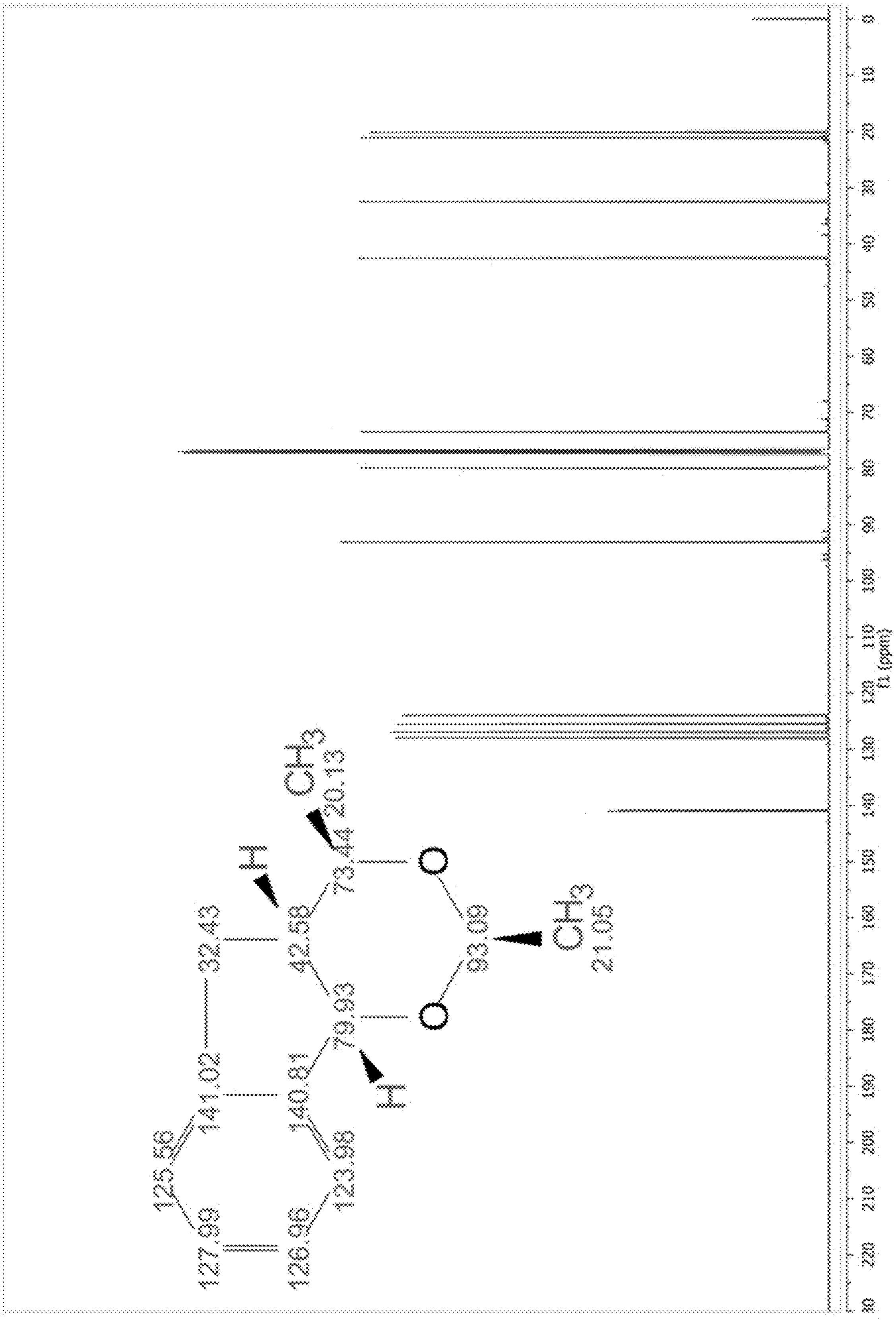
FIG. 2 shows the $^{13}$C-NMR spectrum (151 MHz, $CDCl_3$) of a first diastereomer-enriched odorant mixture according to the invention.

In a first aspect, the present invention relates to a distillative process for the preparation of a (preferably racemic) diastereomerically enriched odourant mixture with a floral note comprising compounds of the general formula (A):

Formula (A)

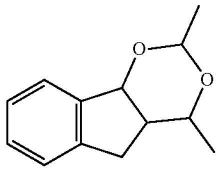, wherein the odorant mixture comprises the following diastereomeric enantiomer pairs:

Enantiomeric pair (I):

Formula (Ia)

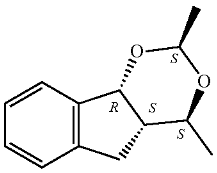

Formula (Ib)

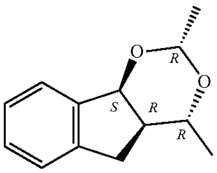

Enantiomeric pair (II):

Formula (IIa)

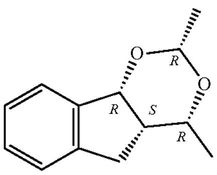

Formula (IIb)

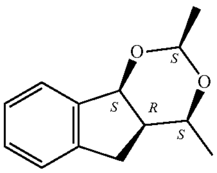

Enantiomeric pair (III):

Formula (IIIa)

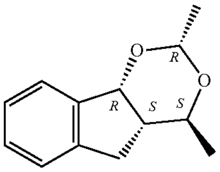

Formula (IIIb)

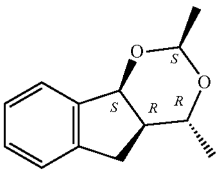

wherein the ratio of the enantiomeric pair (I) and the enantiomeric pair (II) to each other is at least 10:1 and the ratio of the enantiomeric pairs (I) and (III) to each other is at least 50:1, and wherein the process comprises the following distillative steps:

(a) separation by distillation of a crude product comprising compounds of the general formula (A) in a first distillation step;

(b) subsequent fine distillation of the crude product over one or more distillation steps with concentration of the enantiomer pair (I), in particular in relation to the enantiomer pairs (II) and (III), wherein the fine distillation comprises at least 15 separation steps.

The skilled person is aware that the compound of the general formula (A) is a chiral compound. Furthermore, the person skilled in the art is familiar with the fact that these pairs of enantiomers are diastereomeric to each other, while the enantiomers of the pair of enantiomers, as the name already indicates, are enantiomeric to each other, i.e. they behave like image and mirror image. An enrichment of a diastereomer thus means the production of a quantitative excess of one of these enantiomer pairs, here the enantiomer pair (I), relative to the other enantiomer pairs present in the odorant mixture, here the enantiomer pairs (II) and (III) of the general formula (A).

The term "diastereomerically enriched" in this context therefore refers to the proportion of a diastereomer, i.e. a preferred enantiomeric pair, in the mixture with the other possible diastereomers of the compound under consideration, i.e. of the general formula (A). The term "diastereomerically enriched" should be understood to mean that the odorant mixtures obtainable in the process described herein have a significantly higher content of enantiomeric pair (I) relative to the diastereomeric enantiomeric pairs (II) and (III) than the magnolane products obtainable by conventional methods and sold commercially. Consequently, the term "diastereomerically enriched" in the context of the invention describes the presence of a diastereomer, i.e. enantiomeric pair (preferably of enantiomeric pair (I)), as previously defined, with a proportion in the mixture with the other possible diastereomeric isomers in a range of >50% by weight and 100% by weight. In particular, the term "diastereomerically enriched odorant mixture" is to be understood as one which contains at least 80% by weight to 99.9% by weight, preferably 90% by weight to 99.8% by weight and particularly preferably 95% by weight to 99.5% by weight, of the enantiomeric pair (I) comprising the enantiomers of the formulae (Ia) and (Ib), in addition to together up to 20% by weight, preferably up to 10% by weight, and particularly preferably 5% by weight to 0.5% by weight of the further enantiomer pairs (II) and/or (III) diastereomeric thereto.

In the context of the present invention, the term "compounds of formula (I)" or "pair of enantiomers of formula (I)" or "pair of enantiomers (I)", "compound (I)" as well as "isomer (I)" are understood to mean both the individual enantiomeric compounds of formula (I) and consequently the enantiomers (Ia) and (Ib) as well as all mixtures of these enantiomers in any mixing ratio. That is, statements in the following description concerning the "pair of enantiomers (I)" apply both to a single compound of formula (I) and thus the enantiomers (Ia) and (Ib) and to mixtures consisting of or comprising the enantiomers (Ia) and (Ib) in any mixing ratio. The same applies to the designations "pair of enantiomers (II)" and "pair of enantiomers (III)".

However, the enantiomers (Ia) and (Ib), (IIa) and (IIb) as well as (IIIa) and (IIIb) are preferably comprised in relation to each other in such a way that the enantiomer pairs (I), (II) and (III) are present in a racemic mixture of the respective enantiomers (Ia) and (Ib), (IIa) and (IIb) or (IIIa) and (IIIb). Consequently, a further preferred embodiment relates to the provision of a racemic diastereomer-enriched odorant mixture, wherein the enantiomer pairs (I), (II) and (III) are each present in racemic form, but in particular the enantiomer pair (I). Such racemic compounds and consequently racemic diastereomerically enriched odorant mixtures exhibit a particularly balanced and harmonious odour.

The compounds of the general formula (A) have the following designations:

Enantiomeric Pair (I):

Enantiomer (Ia):

(2S,4S,4aS,9bR)-2,4-dimethyl-4,4a,5,9b-tetrahydroindeno[1,2-d][1,3]dioxine

Enantiomer (Ib):

(2R,4R,4aR,9bS)-2,4-dimethyl-4,4a,5,9b-tetrahydroindeno[1,2-d][1,3]dioxine

Enantiomeric pair (II):

Enantiomer (IIa):

(2R,4R,4aS,9bR)-2,4-dimethyl-4,4a,5,9b-tetrahydroindeno[1,2-d][1,3]dioxine

Enantiomer (IIb):

(2S,4S,4aR,9bS)-2,4-dimethyl-4,4a,5,9b-tetrahydroindeno[1,2-d][1,3]dioxine

Enantiomeric pair (III):

Enantiomer (IIIa):

(2R,4S,4aS,9bR)-2,4-dimethyl-4,4a,5,9b-tetrahydroindeno[1,2-d][1,3]dioxine

Enantiomer (IIIb):

(2S,4R,4aR,9bS)-2,4-dimethyl-4,4a,5,9b-tetrahydroindeno[1,2-d][1,3]dioxine

The resulting (preferably racemic) diastereomerically enriched odorant mixture comprising the compounds of the general formula (I) comprises the enantiomer pair (I) relative to the enantiomer pair (II) in the mixture in a ratio of at least 10:1. Preferably, the ratio of the enantiomeric pair (I) and the enantiomeric pair (II) in the mixture to each other is at least 15:1, more preferably at least 20:1, even more preferably at least 50:1. Further preferably, the ratio of these diastereomeric enantiomeric pairs to each other is at least 100:1.

As described in DE 1 793 310, the 2,6-dialkyl-4,5-indano-1,3-dioxane comprises two main geometric isomers, which are present in a ratio of only 1.8:1 to each other. Taken by itself, the Prins reaction can basically be regarded as a very non-selective process, which usually leads to the formation of the enantiomer pairs in almost equal amounts.

In the context of the present invention, it has surprisingly been shown that one of these isomers, however, which normally accrue in the conventional magnolan synthesis in an almost statistical distribution, is to be preferred perfumistically. By means of the process described herein, it is possible to enrich the preferred isomer, isomer (I), in the resulting odorant mixture significantly compared to the second main isomer and thus to positively influence the olfactory properties of the resulting odorant.

Thus, by means of the present method, it was possible to enrich the proportion of the preferred isomer in the rich substance mixture to more than 95% by weight in relation to the other isomers contained and thus to clearly emphasise the positive odour components of the fragrance mixture. It has further been surprisingly shown that especially the compounds of the enantiomer pair (I) are responsible for the positive odour traits of the fragrance mixture and that the above-described isomer distribution enables the production of a particularly intensely floral, "clean" and balanced odour, while the process described herein is as such highly selective, efficient and gentle.

A further embodiment of the method described herein thus relates to the provision of a diastereomer-enriched odorant mixture as described above, wherein the proportion of enantiomer pair (I) in the odorant mixture is at least 95% by weight and more preferably at least 97.5% by weight, even more preferably at least 98.5% by weight based on the sum of enantiomer pairs (I), (II) and (III). Such a fragrance blend exhibits an extremely pleasant and intensely floral odour profile, wherein no technical or otherwise in any way perceived negative odour notes are discernible, i.e. a "clean" intensely floral odour profile.

Accordingly, a further embodiment of the present method of preparation relates to the provision of a diastereomer-enriched odorant mixture, wherein at least 95% by weight of the (preferably racemic) enantiomer pair (I) is comprised, preferably 97.5% by weight, more preferably at least 98.5% by weight based on the sum of the enantiomer pairs (I), (II) and (III).

Such pure or highly enriched diastereomer-enriched fragrance mixtures of the magnolane type are not known to date. Furthermore, it should be emphasised that such a fragrance mixture has been found to have a particularly well-balanced and particularly natural warm and floral odour. It should also be emphasised that the process described herein is a highly selective process which is at the same time particularly gentle.

Furthermore, it was surprisingly found that racemic enantiomer pairs, in particular racemic enantiomer pairs of formula (I), contribute decisively to a balanced, natural, floral and intense odour profile. Thus, it was observed that diastereomerically enriched odorant mixture as described herein, comprising the compounds of general formula (A) and in particular higher proportions of racemic enantiomeric pair (I) compared to enantiomeric pairs (II) and/or (III), contribute to this exceptional odor profile: Thus, the resulting product was found to have a positive and optimised, natural, intensely floral, rosy, transparent, slightly warmer, radiant and geranium-scented odour, showing no technical and plastic-like nuances. In particular, the balanced, intense, exceptionally natural and "clean" floral odour nuances characterise the present fragrance mixture, which can be attributed to the diastereomeric enrichment with the preferably racemic enantiomer pair (I) in the fragrance mixture of the first aspect and establish the suitability of the present fragrance mixture as an odorant or odorant base in a variety of complex odorant preparations and perfumed products.

Moreover, the odorant mixture thus obtained, comprising the compounds of general formula (A), comprises the enantiomeric pairs (I) and (III) preferably in a quantitative ratio to each other of at least 50:1. Further preferably, the quantitative ratio of the enantiomeric pairs (I) and (III) to each other is at least 100:1; more preferably at least 1000:1 and most preferably the corresponding quantitative ratio is at least 1360:1.

At the same time, it was possible to significantly minimise the odorant component that was primarily responsible for the technical and plastic-smelling odour impression and consequently to optimise the odorant mixture accordingly.

Accordingly, the present odorant mixture preferably has a significantly higher proportion of the enantiomers (Ia) and (Ib) of the enantiomer pair (I) relative to the other diastereomers in the odorant mixture, i.e. the enantiomers (IIa) and (IIb) as well as (IIIa) and (IIIb) of the enantiomer pairs (II) and (III).

Surprisingly, it has been found in the context of the present invention that, consequently, by means of the process described herein, diastereomerically enriched odorant mixtures can be obtained at enantiomer pair (I) (preferably racemic), which have an intense and naturally floral, rosy, generally somewhat warmer, transparent and radiant geranium-scented odour profile and are perceived as less technical and do not exhibit plastic-like odour notes (and thus are perceived as "cleaner") compared to commercially available magnolan. Consequently, the smell is more intense, natural, balanced, floral and "cleaner" compared to commercially available Magnolan.

The process steps (a) and (b) of the distillative process for the production of a (preferably racemic) diastereomer-enriched odorant mixture are explained in more detail below.

A first step (a) of the distillation process described herein concerns the separation by distillation of a crude product comprising compounds of the general formula (A). The product subjected to this first distillation step is a crude magnolan product, preferably obtained from the synthesis starting from indene and paraldehyde. The provision of such a product is described further below. Generally, however, it is a magnolan product which has not been subjected to any additional purifying step and which is present as such directly following the reaction of the reactants in the reaction mixture.

The primary purpose of this first distillation step is coarse distillation in order to separate any solvent residues, catalyst residues and unreacted starting compounds or reactants from the essentially not yet diastereomerically enriched odorant mixture comprising the compounds of formula (A) or the enantiomer pairs (I), (II) and (III). If necessary, this process step is also carried out under reduced pressure.

Based on this first distillation step of the process, it is thus possible to provide the fragrance mixture first by separating a magnolan crude product in sufficient chemical purity, in the form of a crude product, and to avoid chemical interactions with other substances contained in the crude product, which could have a negative effect on the overall olfactory impression of the final diastereomer-enriched fragrance mixture.

The crude product comprising compounds of the general formula (A) has, for example, a chemical purity of at least 80%, preferably of at least 90%, following the coarse distillation.

Following this first distillation step, the process described herein for the production of a diastereomer-enriched odorant mixture comprises a further distillation step, the fine distillation of the crude product comprising compounds of the general formula (A). This fine distillation is carried out over one or more distillation steps with concentration of the enantiomer pair (I), wherein the fine distillation comprises at least 15 separation stages. Preferably, however, the fine distillation comprises at least 18 separation stages and most preferably at least 20 separation stages.

The magnolan of formula (A) obtainable by ordinary synthesis usually has a composition in which the isomers (I) and (II) are almost statistically distributed relative to each other, but at most in a ratio of 2:1.

Accordingly, the distillative process to be carried out according to steps (a) and (b) in accordance with the invention also enables the preparation of diastereomer-enriched odorant mixtures by selective fine distillation from an essentially non-diastereomer-enriched starting compound which basically has neither an appreciable enantiomeric nor an appreciable diastereomeric excess of one or more of the geometric isomers contained therein.

Preferably, the preliminary run of the coarse distillation is subjected to the subsequent fine distillation. In this way, even higher (diastereomeric) purities and yields can be achieved.

Furthermore, the process described herein is excellently suited for the large-scale preparation of the fragrance mixture and thus makes it possible to completely cover the needs of the perfume industry. Of particular importance is the consistent quality of the product from batch to batch, which can be guaranteed with the present process. The process shows a particularly high selectivity, requires only a few process steps and is particularly gentle, so that any decomposition or side reactions can be effectively prevented. Consequently, the process described herein is a particularly efficient process.

In particular, enrichments of the enantiomeric pair (I) with a proportion of more than 95 wt. % relative to the sum of the enantiomeric pairs (I), (II) and (III) are thus possible in the resulting odorant mixture.

This enrichment is surprising, as no selective enrichments of the enantiomer pair (I) towards the enantiomer pairs (II) or (III) have been known so far, nor are they to be expected.

In another preferred embodiment, the present invention relates to a process for the preparation of a diastereomer-enriched odorant blend as previously described, which further comprises, prior to the distillative steps (coarse and fine distillation):

the provision of paraldehyde of the general formula (IV) or acetaldehyde,

Formula (IV)

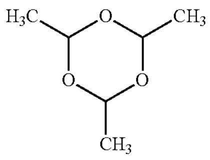

and its reaction with indene of the general formula (V) under acid catalysis in the solvent, Formula (V)

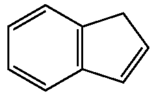

wherein the reaction of the paraldehyde or acetaldehyde with indene takes place at temperatures below 10° C.; and Recovery of the crude product comprising compounds of the general formula (A).

Consequently, this preferred embodiment describes the synthesis of the crude magnolan product which can be subjected to the distillative process of the first aspect and preferably which is also subjected to the distillative process of the first aspect.

In a further embodiment of this synthesis, the reaction of the compounds of the general formulae (IV) and (V) is carried out under acid catalysis, preferably in the presence of dilute sulphuric acid in toluene.

Essentially, the mechanism of the synthesis corresponds to the basic features of the so-called classical Prins reaction, i.e. an acid-catalysed carbonyl-ene reaction, a form of cycloadditions which describes the electrophilic addition of an aldehyde or ketone to an alkene or alkyne.

Consequently, the process described herein further relates to the provision of the crude product (2,4,4a,9b)-2,4-dimethyl-(4,4a,5,9b)-tetrahydroneindeno[1,2d][1,3]dioxin by classical Prins reaction under optimised process conditions.

The conversion of the compounds of formulae (IV) and (V) of the process according to the invention according to the first aspect to the crude product of the general formula (A) is preferably carried out over a period of about 5 hours. Furthermore, it is preferred that the acid catalysis is carried out by reaction in an emulsion of dilute sulphuric acid and toluene.

With this method, very high chemical purities and yields could already be achieved with regard to the (not yet diastereomer-enriched) crude product.

Preferably, no other substances such as antioxidants, iodine, enzymes or other salts are involved in the reaction.

As such, this reaction step of the reactants does not exhibit any selectivity with regard to the individual enantiomeric or diastereomeric isomers of the compounds of the general formula (A). Typically, the crude product of formula (A) is present as a mixture of an essentially statistically distributed amount of the individual geometric isomers, i.e. the enantiomer pairs (I), (II) and (III) are almost statistically distributed in the crude product of general formula (A).

The enantiomers and (preferably racemic) diastereomers mainly formed can be described by the formulae (Ia), (Ib), (IIa), (IIb), (IIIa) and (IIIb) or (I), (II) and (III).

It was found that the diastereomeric enantiomer pairs (I), (II) and (III) have different odour profiles. Thus, the odour of the enantiomer pair (I) can be described as floral, rosy, transparent, radiant and smelling of geranium, while the enantiomer pair (II) gives a floral, green, somewhat technical, grapefruit-smelling odour impression and is weaker compared to the enantiomer pair (I). Furthermore, the enantiomer pair (III) was surprisingly found to have a floral, technical, unclean and plastic-smelling odour profile. An odour description of this enantiomer pair (III) could now be identified and described for the first time in the context of the present invention.

Furthermore, it has been shown that isomer (I) is the most odoriferously valuable isomer of the three identified mutually diastereomeric isomers, so that the diastereomer-selective enrichment of the odorant mixture with the geometric isomers of the preferably racemic enantiomer pair (I) is particularly desirable and there is a need for an efficient and selective process to enrich in particular the isomers of the enantiomer pair (I) in the odorant mixture to be prepared.

At the same time, a reduction of the proportion of the enantiomer pair (III) is thus preferred with regard to the odour characteristics perceived as negative. It is of particular interest that the quantity ratio of the enantiomer pairs (I) and (III) to each other is at least 50:1.

At the same time, or independently thereof, it is further desirable that the quantitative ratio of the enantiomer pair (I) and the enantiomer pair (II) to each other is at least 10:1.

It was surprisingly found that when the diastereomeric enantiomer pairs (I), (II) and (III) are present in these ratios to each other, particularly intense radiant, warmer, more natural, and transparent floral or floral odour profiles can be obtained for the corresponding fragrance blends, which exhibit a particular balance.

However, standard methods for isolating an enantiomer or diastereomer or enantiomer pair usually involve a large number of intermediate steps, such as the targeted provision of certain reactants in form of predetermined stereoisomers or the enzymatic control of the geometry. Furthermore, such methods are usually neither gentle nor particularly efficient or selective in their entirety.

However, with the process described herein for the preparation of a (preferably racemically) diastereomerically enriched odorant mixture comprising the compounds of the general formula (A) and the enantiomer pairs (I), (II) and (III) it has been successful to enrich the proportion of the enantiomeric pair (I) relative to its diastereomers in such a way that the resulting product exudes a positive and optimised, natural, intensely floral, rosy, transparent, somewhat warmer, radiant and geranium-smelling odour. In particular, the high intensity, cleanliness and naturalness of the odour distinguish the present fragrance blend as an excellent odorant/odorant blend or base for further use in the manufacture of natural and intensely floral-smelling fragrance preparations and perfumed products. In combination with the reduced technical, impure and plastic-smelling nuances, this results in an excellent fragrance blend with an exceptional, balanced, intense and "clean" floral odour, which can be excellently incorporated into complex fragrance creations. These odour nuances can be achieved with fragrance mixtures containing the enantiomer pairs (I), (II) and (III) in the ratios according to the invention. A certain proportion of enantiomeric pair (II) in the odorant mixture may also contribute to a more intensely floral, greener and thus more natural floral component. Natural nuances are of particular interest in the perfume industry. Thus, the fragrance mixture described above can provide the perfume industry with a fragrance component that is particularly suitable as a natural floral fragrance component in various preparations and products due to its particularly intense, floral, balanced and surprisingly "clean" odour profile.

Furthermore, a highly selective, simple and gentle manufacturing process has now been developed, which makes it possible to produce an optimised intensive floral odorant in just a few steps and thus to provide it at the same time cost-effective, extremely pure and in high yield.

At the same time, the method described herein enables efficient and highly selective diastereomer enrichment of the enantiomer pair (I) starting from the synthesis of the crude product by means of classical Prins reaction in high yields and in high product purity.

It was also found that the process described herein can be used to produce fragrance blends that have a floral, rosy, transparent, radiant odour reminiscent of geranium. The diastereomer-enriched odorant mixtures produced in this way do not exhibit any technical odour notes or odour notes reminiscent of plastic. The smell of grapefruit also recedes clearly into the background, so that the fragrance mixture produced in this way essentially has a much more radiant, intense and natural floral olfactory impression than commercially available magnolan products.

In a further preferred alternative, the process described herein for producing a diastereomer-enriched odorant mixture according to the first aspect is carried out such that the fine distillation of the distillative process is carried out in a continuous process.

This continuous process makes it possible to reduce the number of intermediate steps, such as refilling or cooling and heating the apparatus, and is therefore more economical compared to so-called batch processes and ensures a constant, i.e. consistent, product quality. Accordingly, the present process is also suitable for the production of the described fragrance mixture on an industrial scale and thus allows the high-quality production of the diastereomer-enriched fragrance mixture in quantities of more than 180 kg with excellent fragrance properties and outstanding purity.

In a further preferred embodiment, the step of fine distillation in the distillative process according to the invention according to the first aspect for producing a diastereomer-enriched odorant mixture is carried out at a reflux ratio of at least 5:1. Preferably, said reflux ratio is at least 7:1 and most preferably at least 10:1 in order to achieve particularly high proportions of the enantiomer pair (I) relative to the enantiomer pairs (II) and (III) and to minimise the odour components described as negative and technical or smelling of plastic, while the intense floral and positive odour impressions come to the fore.

In the context of the present invention, it was surprisingly found that such a reflux ratio in combination with the previously described parameters leads to a particularly efficient and strong diastereomeric enrichment of the enantiomeric pair (I) in the odorant mixture described herein.

Further preferably, in the process according to the invention according to the first aspect, the fine distillation of the distillative process is carried out at temperatures between 120° C. and 150° C., but preferably the overhead temperature is between 125° C. and 145° C., more preferably between 135° C. and 140° C.

This enables efficient and highly selective enrichment of the preferred diastereomer, i.e. the enantiomeric pair (I), and ensures reproducibility of the desired odour profile.

In a further preferred embodiment, the fine distillation of the distillative process described herein for producing a diastereomer-enriched odorant mixture is carried out at a reduced pressure of about 1 mbar to 100 mbar, preferably at a reduced pressure of about 1 mbar to 50 mbar, more preferably at a reduced pressure of about 1 mbar to 10 mbar and even more preferably at a reduced pressure of 10 mbar.

Such a process enables the particularly efficient and gentle enrichment of the enantiomer pair (I) as described herein. A particularly gentle enrichment is of great importance, since unwanted decompositions can thus be reduced. Thus, in the present invention, gentle enrichment means that both thermal and pressure stress during diastereomer enrichment are low and the diastereomer-enriched odorant mixture produced therefrom does not suffer any negative thermal or pressure damage in the process, which may manifest itself in decomposition or a change in product properties such as colour, odour, stability etc. due to the formation of decomposition and by-products. Such decomposition and by-products could interact adversely with the odorant or odorant mixture and thus reduce the overall product quality by, for example, causing unpleasant secondary odours which distort or adversely affect the characteristic odour impression of the odorant or odorant mixture or even have an adverse effect on the stability of the odorant s and odorant mixtures or of the preparations and products containing the rich substances and rich substance mixtures.

Furthermore, the present invention relates to a process for preparing a diastereomer-enriched odorant mixture according to the first aspect, wherein the first coarse distillation step (a) describes a thin film distillation.

The process according to the invention is therefore particularly suitable for the efficient production of highly diastereomer-enriched and pure odorants or odorant mixtures in high yields through the combination of gentle and selective production under mild conditions, which have an optimised particularly intense, balanced and natural floral odour. Temperature-sensitive substances, such as many odorants and/or flavourings, may generally only be heated to high temperatures for a short time in order to counteract unwanted thermal decomposition processes. Classical distillation processes usually lead to a long thermal load on the component to be distilled, which can negatively influence both the yield and the quality of the products obtained. Efficient distillation processes with high selectivity, i.e. high separation efficiency and at the same time short residence times, are therefore particularly preferred for enrichment. Since the thin film evaporator in the present invention is preferably operated in a vacuum, the process described herein allows the use of lower temperatures and is therefore suitable for particularly gentle separation of the crude product as described herein. Thus, the process according to the invention is characterised in its entirety as a very gentle process which reduces unwanted thermal and pressure-related decomposition and with the aid of which the crude product can already be isolated efficiently and gently in very high purities and yields, i.e. with excellent product quality.

In addition, a further preferred embodiment of the process described herein for producing a diastereomer-enriched odorant mixture of the first aspect relates to a thin film distillation comprising two stages:

separating the solvent at a reduced pressure of about 1 mbar to 400 mbar, preferably at a reduced pressure of about 100 mbar to 300 mbar, more preferably at a reduced pressure of about 150 mbar to 250 mbar and even more preferably at a reduced pressure of about 200 mbar; and Extraction of the crude product comprising compounds of the general formula (A) at a reduced pressure of about 0 mbar to 100 mbar, preferably at a reduced pressure of about 0 mbar to 10 mbar, more preferably at a reduced pressure of about 0 mbar to 5 mbar; even more preferably at a reduced pressure of about 1 mbar.

Furthermore, in a particularly preferred embodiment of the process, the first stage of the thin film distillation is carried out at a shell temperature of between 120° C. and 200° C., but preferably at temperatures between 150° C. and 180° C., more preferably at temperatures between 160° C. and 175° C., and particularly preferably at a temperature of about 165° C., and the second stage of the thin film distillation is carried out at a jacket temperature of between 150° C. and 250° C., but preferably at temperatures between 180° C. and 210° C., even more preferably at temperatures between 185° C. and 200° C. and particularly preferably at a temperature of about 190° C.

In this way, an even gentler and more efficient extraction of the Magnolan crude product can be achieved in terms of purity and yield.

In a second aspect, the present invention comprises a (preferably racemic) diastereomer-enriched odorant composition comprising compounds of the general formula (A):

Formula (A)

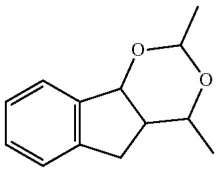

wherein the compounds of formula (A) comprise the following mutually diastereomeric enantiomer pairs of formulae (I), (II) and (III):

Enantiomeric pair (I):

Formula (Ia)

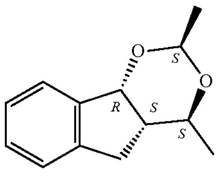

-continued

Formula (Ib)

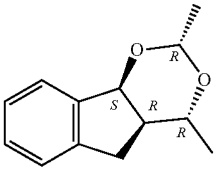

Enantiomeric pair (II):

Formula (IIa)

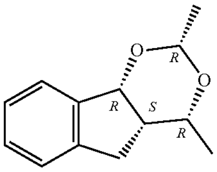

Formula (IIb)

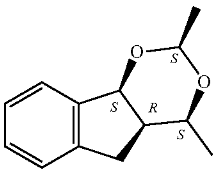

Enantiomeric pair (III):

Formula (IIIa)

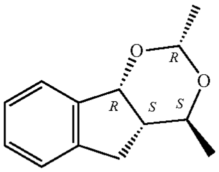

Formula (IIIb)

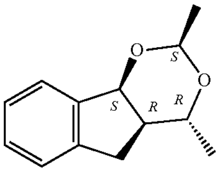

wherein the ratio of the enantiomeric pair (I) and the enantiomeric pair (II) to each other is at least 10:1 and the ratio of the enantiomeric pairs (I) and (III) to each other is at least 50:1.

The (preferably racemic) diastereomerically enriched odorant mixture of the second aspect, comprising the compounds of the general formula (A), comprises the enantiomer pair (I) relative to the enantiomer pair (II) in the mixture in a ratio of at least 10:1. Preferably, the ratio of the enantiomeric pair (I) and the enantiomeric pair (II) in the mixture to each other is at least 15:1, more preferably at least 20:1, even more preferably at least 50:1. Further preferably, the ratio of these diastereomeric enantiomeric pairs to each other is at least 100:1.

Furthermore, the (preferably racemic) diastereomerically enriched odorant composition of the second aspect of the present invention comprising the compounds of general formula (A) comprises the enantiomeric pairs (I) and (III) to each other preferably in a ratio of at least 50:1. Further preferably, the ratio of the enantiomeric pairs (I) and (III) to each other is at least 100:1; more preferably at least 1000:1 and most preferably at least 1360:1.

The diastereomer-enriched odorant blend preparable by the method of the first aspect has an intense floral, natural, rosy, transparent and radiant geranium-scented odour, which is perceived as less technical than commercially available magnolan and does not exhibit odour notes reminiscent of plastic, i.e. is "cleaner".

Accordingly, diastereomer-enriched odorant mixtures of the general formula (A) which have a higher proportion of the enantiomer pair (I) relative to the enantiomer pairs (II) and/or (III) are favourable in the sense of the present invention, particularly preferably in a ratio of enantiomer pair (I) to enantiomer pair (II) of at least 10:1 and a ratio of enantiomer pair (I) to enantiomer pair (III) of at least 50:1 in the odorant mixture. Such odorant mixtures exhibit enhanced floral, natural, "clean", rosy, transparent and radiant geranium-scented odour profiles. Further preferred are the proportions as defined above.

In a further preferred embodiment, the diastereomer-enriched fragrance blend preferably has the enantiomer pair (I) in the rich blend in a proportion greater than 95% by weight (compared to all enantiomer pairs in the fragrance blend) which results in the positive odour components of the fragrance blend being clearly emphasised. Such a fragrance blend also exhibits an extremely pleasant and intensely floral and natural odour profile, wherein no technical or otherwise in any way negatively perceived odour notes are discernible.

A further embodiment of the present diastereomer-enriched odorant mixture therefore concerns a odorant mixture comprising at least 95% by weight (compared to all enantiomer pairs) of the (preferably racemic) enantiomer pair (I). Preferably the proportion of enantiomeric pair (I) is at least 97.5% by weight and even more preferably at least 98.5% by weight relative to the sum of enantiomeric pairs (I), (II) and (III) of the odorant mixture according to the invention, so that particularly intense floral, "clean" and natural odour impressions can be achieved.

Furthermore, the diastereomer-enriched fragrance mixture shows high purity and can be provided in very high yield.

Accordingly, in another preferred embodiment, the present invention relates to the diastereomer-enriched odorant blend of the second aspect, wherein the odorant blend comprises an overall chemical purity of at least 96.5% by weight of enantiomer pairs (I), (II) and (III), but preferably at least 98.5% by weight, most preferably at least 99.0% by weight.

Such fragrance blends have excellent secondary properties, such as high stability.

In a further optional embodiment, the remainder of the diastereomer-enriched odorant mixture constitutes further impurities, the odorant mixture according to the invention, however, containing less than 3.0% by weight, preferably less than 2.0% by weight of such impurities, preferably at most or less than 1.5% by weight, most preferably at most 1.0% by weight of such impurities, based on the total mass of the odorant mixture.

The diastereomer-enriched fragrance mixtures are suitable as odorant s or as additives of fragrance preparations. Further uses of these diastereomer-enriched fragrance mixtures are in consumer products containing these compounds and mixtures.

In a third aspect, the present invention relates to the use of the diastereomer-enriched odorant mixture as an odorant or for the preparation of an odorant composition. Thus, the present invention relates to the use of the odorant mixture according to the invention as an odorant, in particular with an optimised, intensely radiant, natural and transparent floral fragrance, or for the preparation of an odorant composition, in particular with such an optimised floral fragrance profile.

Another aspect of the present invention thus relates to an odorant preparation comprising a sensory effective amount of the diastereomer-enriched odorant mixture as defined above.

In the context of the present invention, a fragrance preparation is a mixture of different substances which is produced from the corresponding substances according to a recipe or formulation in accordance with a predetermined process. Such preparations are made and used specifically for the purpose of imparting, modifying or enhancing a desired odour impression which is usually perceived as pleasant or otherwise positive.

A fragrance preparation according to the invention, in particular in the form of a perfume oil, preferably with an optimised floral odour note as described herein, consists of or comprises the diastereomer-enriched fragrance mixture according to the invention, as defined above, and one, two, three, four, five, six, seven, eight, nine, ten or more further odorant (s). In this way, it is easy to create mixtures with particularly interesting, intense and natural floral odour notes, which do not have technical or plastic-like odour notes like most previous magnolan-based odorant preparations. The fragrance mixtures according to the invention can be used as a single substance or combined with a variety of other odorant s in numerous products in order to create or generate a special olfactory impression.

Odorant s and/or flavouring substances which are suitable for use in a fragrance preparation according to the invention as further odorant s or flavouring substances in the sense of the above definition can be found, for example, in S. Arctander, "Perfume and Flavor Materials", Vol. I and II, Montclair, N. J. 1969, self-published, or K. Bauer et al, "Common Fragrance and Flavor Materials", 4th Edition, Wiley-VCH, Weinheim 2001.

In detail, we would like to mention: Extracts from natural raw materials such as essential oils, concretes, absolutes, resins, resinoids, balsams, tinctures such as. ambergris oil; *amyris* oil; *angelica* seed oil; *angelica* root oil; anise oil; valerian oil; basil oil; tree moss absolute; bay oil; mugwort oil; benzoeresin; bergamot oil; beeswax absolute; birch tar oil; bitter almond oil; savory oil; bucco leaf oil; cabreuva oil; cade oil; calmus oil; Camphor oil; *Cananga* oil; *Cardamom* oil; *Cascarilla* oil; *Cassia* oil; Cassie absolute; *Castoreum* absolute; Cedar leaf oil; Cedarwood oil; *Cistus* oil; *Citronella* oil; Citron oil; *Copaiva* balsam; *Copaiva* balsam oil; Coriander oil; *Costus* root oil; Cumin oil; Cypress oil; *Davana* oil; Dill herb oil; Dill seed oil; Eau de brouts absolute; Oak moss absolute; Elemi oil; Tarragon oil; *Eucalyptus citriodora* oil; *Eucalyptus* oil; Fennel oil; Spruce needle oil; *Galbanum* oil; *Galbanum* resin; Geranium oil; Grapefruit oil; Guaiac wood oil; Gurjun balsam; Gurjun balsam oil; *Helichrysum* absolute; *Helichrysum* oil; Ginger oil; *Iris* root absolute; *Iris* root oil; Jasmine absolute; *Calamus* oil; Camomile oil blue; Camomile oil Roman; Carrot seed oil; *Cascarilla* oil; *Pine* needle oil; Curly mint oil; Caraway seed oil; Labdanum oil; Labdanum absolute; Labdanum resin; Lavandin absolute; Lavandin oil; Lavender absolute; Lavender oil; Lemongrass oil; Lovage oil; Lime oil distilled; Lime oil pressed; Linaloe oil; *Litsea cubeba* oil; Bay leaf oil; Mace oil; Marjoram oil; *Mandarin* oil; Masso bark oil; *Mimosa* absolute; Musk grain oil; Musk tincture; Clary sage oil; *Muscat* oil; Myrrh absolute; Myrrh oil; Myrtle oil; Clove leaf oil; Clove flower oil; Neroli oil; Olibanum absolute; Olibanum oil; *Opopanax* oil; Orange flower absolute; Orange oil; *Origanum* oil; Palmarosa oil; Patchouli oil; *Perilla* oil; *Peru* balsam oil; Parsley leaf oil; Parsley seed oil; Petitgrain oil; Peppermint oil; Pepper oil;

Allspice oil; *Pine* oil; Poley oil; Rose absolute; Rosewood oil; Rose oil; Rosemary oil; Sage oil Dalmatian; Sage oil Spanish; Sandalwood oil; Celery seed oil; Spikenard lavender oil; Star anise oil; *Styrax* oil; *Tagetes* oil; Fir needle oil; Tea tree oil; Turpentine oil; Thyme oil; Tolu balsam; Tonka absolute; *Tuberose* absolute; Vanilla extract; Violet leaf absolute; *Verbena* oil; Vetiver oil; Juniper berry oil; Wine yeast oil; Wormwood oil; Wintergreen oil; Ylang oil; Hyssop oil; Civet absolute; Cinnamon leaf oil; Cinnamon bark oil, and fractions thereof or ingredients isolated therefrom;

Individual odorants from the group of hydrocarbons, such as 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

of the aliphatic alcohols such as hexanol; octanol; 3-octanol; 2,6-dimethylheptanol; 2-methyl-2-heptanol; 2-methyl-2-octanol; (E)-2-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

of the aliphatic aldehydes and their acetals, e.g. hexanal; heptanal; octanal; nonanal; decanal; undecanal; dodecanal; 2-methyloctanal; 2-methylnonanal; (E)-2-hexenal; (Z)-4-heptenal; 2,6-di methyl-5-heptenal; 10-undecenal; (E)-4-decenal; 2-dodecenal; 2,6,10-trimethyl-9-undecenal; 2,6,10-trimethyl-5,9-undecadienal; heptanaldiethyl acetal; 1,1-dimethoxy-2,2,5-trimethyl-4-hexene; citronellyloxy-acetaldehyde; 1-(1-methoxy-propoxy)-(E/Z)-3-hexene;

of aliphatic ketones and their oximes, such as 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

of aliphatic sulphur-containing compounds, such as 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthen-8-thiol;

of aliphatic nitriles, such as 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

of aliphatic carboxylic acids and their esters, such as e.g. (E)- and (Z)-3-hexenyl formate; ethyl acetoacetate; isoamyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octene-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxyacetate; methyl 3,7-dimethyl-2,6-octadieneoate; 4-methyl-2-pentyl crotonate;

the acyclic terpene alcohols, such as e.g. geraniol; nerol; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and their formates, acetates, propionates, isobutyrates, butyrates, isovalerianates, pentanoates, hexanoates, crotonates, tiglinates and 3-methyl-2-butenoates;

of the acyclic terpene aldehydes and ketones, such as citronellal; 7-methoxy-3,7-dimethyloctanal; 2,6,10-trimethyl-9-undecenal; geranylacetone; and the dimethyl and diethylacetals of geranial, neral;

of the cyclic terpene alcohols, such as e.g. menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiaol; and their formates, acetates, propionates, isobutyrates, butyrates, isovalerianates, pentanoates, hexanoates, crotonates, tiglinates and 3-methyl-2-butenoates;

of cyclic terpene aldehydes and ketones, such as menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; beta-damascenone; 1-(2,4,4-trimethyl-2-cyclohexen-1-yl)-2-buten-1-one; 1,3,4,6,7,8a-Hexahydro-1,1,5,5-tetramethyl-2H-2,4a-methano-naphthalen-8-(5H)-on; 2-Methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methylcedryl ketone);

of cyclic alcohols, such as 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of the cycloaliphatic alcohols such as alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 3-methyl-5-(2,2,3-trimethyl-3-cyclopent-1-yl)pentan-2-ol; 3-Methyl-5-(2,2,3-trimethyl-3-cyclopent-1-yl)-4-penten-2-ol; 3,3-Dimethyl-5-(2,2,3-trimethyl-3-cyclopent-1-yl)-4-penten-2-ol; 1-(2,2,6-Trimethylcyclohexyl)pentan-3-ol; 1-(2,2,6-Trimethylcyclohexyl)hexan-3-ol;

of the cyclic and cycloaliphatic ethers, such as e.g. cineol; cedryl methyl ether; cyclododecyl methyl ether; 1,1-dimethoxycyclododecane; (ethoxymethoxy)-cyclododecane; alpha-cedrene epoxide; 3a,6,6,9a-tetramethyl-dodecahydro-naphtho[2,1b]furan; 3a-ethyl-6,6,9a-trimethyldodecahydronaphtho[2,1b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of cyclic and macrocyclic ketones such as 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

of cycloaliphatic aldehydes, such as 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

of the cycloaliphatic ketones, such as 1-(3,3-Dimethylcyclohexyl)-4-penten-1-one; 2,2-Dimethyl-1-(2,4-dimethyl-3-cyclohexen-1-yl)-1-propanone; 1-(5,5-Dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert.-butyl-(2,4-dimethyl-3-cyclohexen-1-yl)ketone;

the esters of cyclic alcohols, such as 2-tert-butylcyclohexyl acetate; 4-tert-butylcyclohexyl acetate; 2-tert-pentylcyclohexyl acetate; 4-tert-pentyl cyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5, resp. 6-indenyl acetate; 4,7-methano-3a,4,5,6,7,7a-hexahydro-5, or 6-indenyl propionate; 4,7-methano-3a,4,5,6,7,7a-hexahydro-5, or 6-indenyl isobutyrate; 4,7-methanooctahydro-5, or 6-indenyl acetate;

the esters of cycloaliphatic alcohols, such as 1-cyclohexylethyl crotonate;

the esters of cycloaliphatic carboxylic acids, such as allyl 3-cyclohexyl propionate; allyl cyclohexyloxy acetate; cis- and trans-methyl dihydrojasmonate; cis- and trans-methyl jasmonate; methyl 2-hexyl-3-oxocyclopentane carboxylate; ethyl 2-ethyl-6,6-dimethyl-2-cyclohexene carboxylate; ethyl 2,3,6,6-tetramethyl-2-cyclohexene carboxylate; ethyl 2-methyl-1,3-dioxolane-2-acetate;

of the aliphatic alcohols, such as e.g. benzyl alcohol; 1-phenylethyl alcohol; 3-phenylpropanol; 2-phenylpropanol; 2-phenoxyethanol; 2,2-dimethyl-3-phenyl propanol; 2,2-dimethyl-3-(3-methylphenyl) propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropyl phenyl)ethanol;

the esters of aliphatic alcohols and aliphatic carboxylic acids such as benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethyl benzyl acetate; alpha,alpha-dimethylphenyl ethyl acetate; alpha,alpha-dimethylphenyl ethyl butyrate; cinnamyl acetate; 2-phenoxyethyl isobutyrate; 4-methoxybenzyl acetate;

of aliphatic ethers, such as 2-phenylethyl methyl ether; 2-phenylethyl isoamyl ether; 2-phenylethyl 1-ethoxyethyl ether; phenylacetaldehyde dimethylacetal; phenylacetaldehyde diethylacetal; hydratropaaldehyde dimethylacetal; phenylacetaldehyde glycerol acetal; 2,4,6-trimethyl-4-phenyl-1,3-dioxane;

of the aromatic and aliphatic aldehydes, such as benzaldehyde; phenylacetaldehyde; 3-phenylpropanal; hydratropaaldehyde; 4-methyl benzaldehyde; 4-methyl phenylacetaldehyde; 3-(4-ethyl phenyl)-2,2-di methyl propanal; 2-methyl-3-(4-isopropylphenyl)propanal; 2-methyl-3-(4-isobutyl phenyl) propanal; 3-(4-tert.-butyl phenyl) propanal; cinnamaldehyde; alpha-butylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-di methoxybenzaldehyde; 2-methyl-3-(4-methoxyphenyl)propanal; 2-methyl-3-(4-methylenedioxyphenyl)propanal;

of the aromatic and aliphatic ketones, such as acetophenone; 4-methylacetophenone; 4-methoxyacetophenone; 4-tert.-butyl-2,6-di methylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert.butyl-1,1-di-methyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

of aromatic and aliphatic carboxylic acids and esters thereof, such as benzoic acid; phenylacetic acid; methyl benzoate; ethyl benzoate; hexyl benzoate; benzyl benzoate; methyl phenyl acetate; ethyl phenyl acetate; geranyl phenyl acetate; phenylethyl phenyl acetate; methyl cinnamate; ethyl cinnamate; benzyl cinnamate; phenylethyl cinnamate; cinnamyl cinnamate; allyl phenoxy acetate; methyl salicylate; hexyl salicylate; cyclohexyl salicylate; cis-3-hexenyl salicylate; benzyl salicylate; phenyl ethyl salicylate; methyl 2,4-dihydroxy-3,6-di methyl benzoate; ethyl 3-phenylglycidate; ethyl 3-methyl-3-phenylglycidate;

of nitrogen-containing aromatic compounds, such as 2,4,6-trinitro-1,3-dimethyl-5-tert-butylbenzene; 3,5-dinitro-2,6-dimethyl-4-tert.butylacetophenone; cinnamic acid nitrile; 3-methyl-5-phenyl-2-pentenoic acid nitrile; 3-methyl-5-phenylpentanoic acid nitrile; methyl anthranilate; methyl N-methyl anthranilate; Schiff bases of methyl anthranilate with 7-hydroxy-3,7-dimethyloctanal, 2-methyl-3-(4-tert.-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; scatole; 2-methoxy-3-isopropylpyrazine; 2-isobutyl-3-methoxypyrazine;

of phenols, phenyl ethers and phenyl esters, e.g. tarragol; anethole; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresylphenyl acetate;

of heterocyclic compounds, such as 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of the lactones, such as 1,4-octanolide; 3-methyl-1,4-octanolide; 1,4-nonanolide; 1,4-decanolide; 8-decene-1,4-olide; 1,4-undecanolide; 1,4-dodecanolide; 1,5-decanolide; 1,5-dodecanolide; 4-methyl-1,4-decanolide; 1,15-pentadecanolide; 1,16-hexadecanolide; 9-hexadecene-1,16-olide; 10-oxa-1,16-hexadecanolide; 11-oxa-1,16-hexadecanolide; 12-oxa-1,16-hexadecanolide; ethylene-1,12-dodecanedioate; ethylene-1,13-tridecanedioate; 2,3-dihydrocoumarin; octahydrocoumarin.

In an odorant preparation according to the invention, in particular a perfume oil, the amount of the diastereomer-enriched odorant mixture, as defined above, is in a range from 0.0001% by weight to 40% by weight, preferably in a range from 0.001% by weight to 25% by weight, and particularly preferably in a range from 0.0001% by weight to 10% by weight or 5% by weight, based on the total weight of the odorant preparation.

In addition to use as a liquid in solutions or in emulsions, the odorant mixtures according to the invention or odorant preparations containing these odorant mixtures according to the invention, for example perfume oils, can be used adsorbed on solids or (micro)encapsulated in carriers. These dosage forms can provide both a fine distribution of the odorant s in the product and a controlled release during use. Such solids may be porous inorganic materials such as light sulphate, silica gels, zeolites, gypsums, clays, clay granules, aerated concrete, etc. or organic materials such as woods, cellulose-based materials, sugars or plastics such as PVC, polyvinyl acetates or polyurethanes.

Encapsulation products can be, for example, spray-dried, inclusion complex or extrusion products.

In the context of the present invention, a "sensory effective amount" is understood to mean that the odorant or the diastereomer-enriched odorant blend is present in such a sufficient amount that the resulting product, when used, reveals the sensory properties of the odorant or the odorant blend according to the invention. Thus, a sensory effective amount is to be understood as a proportion of the odorant mixture according to the invention which is sufficient to bring about the effects herein, i.e. for example highlighting or emphasising a pleasant and optimised floral odour note and/or a masking effect.

Further, the present invention thus relates to the use of the diastereomer-enriched odorant composition according to any of the preceding aspects in a sensory effective amount for imparting, modifying or enhancing a floral odour note of a perfumed product or for the preparation of a perfumed product. Enhance in this context means to highlight or emphasise a particular odour note, in particular odours or odour notes of the optimised intense and naturally "clean" floral type as described herein.

Since floral odorants, i.e. odorants with a "clean" floral note, are particularly preferred and in demand in the perfumery industry, the odorant s and odorant preparations comprising the diastereomer-enriched odorant mixture described in the present invention are particularly suitable for such uses. In particular, fragrances of the technical type or those reminiscent of plastic are generally perceived as negative and therefore as disrupting. Since the present odorant mixture can be prepared simply, in a few steps and at the same time in high yield and in high purity, an odorant mixture can be made available which does not have the said odour notes perceived as negative and is thus suitable for a variety of applications, in particular for imparting, modifying or enhancing an intensely radiant and "clean" floral odour note.

In the present case, "clean" is to be understood as an olfactory note which does not have any technical, plastic-like or otherwise negatively perceived odour characteristics which distract from the floral note and are not perceived as natural.

The odorant s or odorant blends and preparations described herein show a clear enhancement of the intense, natural and "clean" floral fragrance notes even at low dosages.

Surprisingly, it was observed that the fragrance mixture described herein has excellent stability properties and is thus eminently suitable for incorporation into a variety of product formulations. Consequently, the present fragrance blend is particularly suitable for the manufacture of a variety of perfumed products, such as shampoos, creams, soaps, deodorants, detergents and the like.

Ultimately, therefore, the present invention relates to a perfumed product comprising the diastereomer-enriched fragrance blend as described above or a corresponding fragrance preparation in concentrated form, in solutions or in other modified form for the manufacture of consumer or perfumed products within the meaning of the invention, such as perfume extracts, eau de parfums, eau de toilettes, shaving waters, eau de colognes, pre-shave products, splash colognes and perfumed products. e.g. perfume extracts, eau de parfums, eau de toilettes, shaving waters, eau de colognes, pre-shave products, splash colognes and perfumed refreshing wipes, as well as for the perfuming of acidic, alkaline and neutral cleaning agents, e.g. Floor cleaners, window glass cleaners, dishwashing detergents, bathroom and sanitary cleaners, scouring agents, solid and liquid WC cleaners, powder and foam carpet cleaners, liquid detergents, powder detergents, laundry pre-treatment agents such as bleaching agents, soaking agents and stain removers, laundry softeners, laundry soaps, laundry tablets, disinfectants, surface disinfectants as well as air fresheners in liquid, gel or solid form, aerosol sprays, waxes and polishes such as furniture polishes, floor waxes, shoe polishes as well as personal care products such as solid and liquid soaps, shower gels, shampoos, shaving soaps, shaving foams, bath oils, cosmetic emulsions of the oil-in-water, water-in-oil and water-in-oil-in-water type such as e.g. skin creams and lotions, facial creams and lotions, sunscreen creams and lotions, after-sun creams and lotions, hand creams and lotions, foot creams and lotions, depilatory creams and lotions, aftershave creams and lotions, tanning creams and lotions, hair care products such as hair sprays, hair gels, hair lotions, hair conditioners, permanent and semi-permanent hair dyes, hair shaping products such as cold waves and hair straighteners, hair tonics, hair creams and lotions, deodorants and antiperspirants such as underarm sprays, roll-ons, deodorant sticks, deodorant creams or products of decorative cosmetics.

Consequently, the present invention also ultimately relates to a perfumed product comprising the diastereomer-enriched odorant blend as described above, or a corresponding odorant preparation comprising the same.

Examples

The present invention is described in more detail below with reference to examples of embodiments.

Preparation of a diastereomer-enriched odorant composition according to the process described herein:

First, an emulsion of diluted sulphuric acid and toluene was placed in a reaction vessel. Then the reactants paraldehyde and indene were added at a temperature of 5° C. and stirred for a period of 5 hours. The reaction product was then washed three times with water and the organic phase distilled off.

According to step (a) of the process described herein, the resulting reaction product was fed to a thin film evaporator. In the first stage of the thin film distillation, the crude product was freed from any solvent residues and unreacted reactants at 200 mbar and a jacket temperature of 165° C. The purified crude product was then removed by distillation at 1 mbar and a jacket temperature of 190° C. (second stage of thin film distillation).

Subsequently, the resulting crude product was subjected to a fine distillation (step (b)). For this purpose, the crude product was distilled in a distillation apparatus with Sulzer BX as the filler material over 20 separation stages in a continuous process. The reflux ratio was about 10:1, the head temperature about 138° C. to 139° C. and the distillation was carried out at a reduced pressure of about 10 mbar.

The product thus obtained has the enantiomeric pairs in the following proportions: the proportion of enantiomeric pair (I) to enantiomeric pair (II) in the odorant mixture obtained is 96.894 to 0.577, while the proportion of enantiomeric pair (I) to enantiomeric pair (III) is 96.894 to 0.047. Consequently, the proportion of the enantiomeric pair (I) compared to the total of the compounds according to formula (A), i.e. based on the sum of the enantiomeric pairs (I), (II) and (III), in the odorant mixture thus obtained is also at least 95% by weight and exhibits a corresponding diastereomeric purity. In this case, the chemical purity, i.e. the sum of all diastereomers of formula (A) in relation to all other impurities was 97.5 to 2.5.

Figure 3:
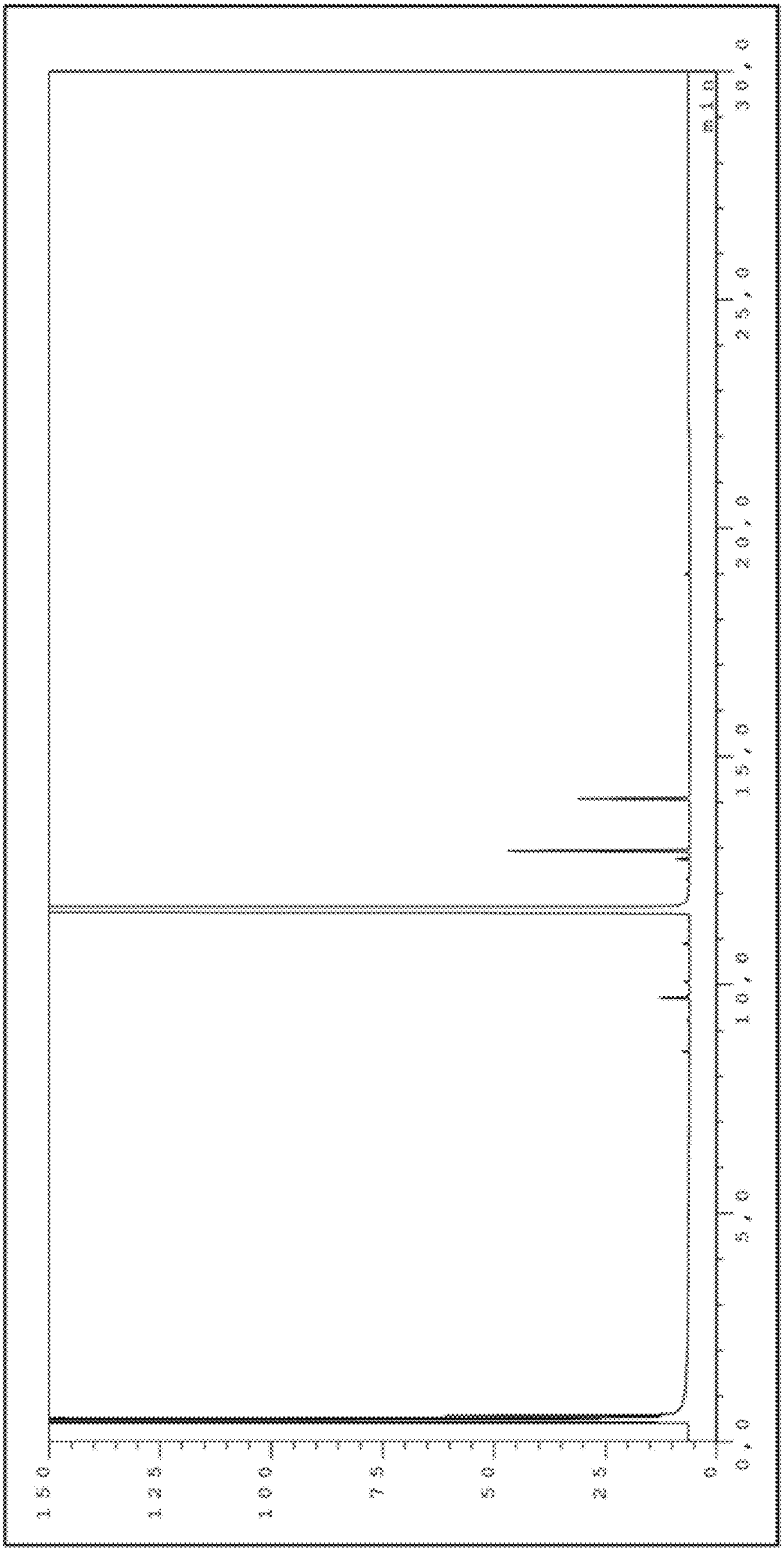
FIG. 3 shows the gas chromatographic analysis of a second diastereomer-enriched odorant mixture according to the invention.

In a further second example using the same method, the ratio of the enantiomer pairs (I) to (II) to (III) was 97.971 to 0.979 to 0.072. Here too, the proportion of the enantiomer pair (I) is over 95 wt. % based on the sum of the enantiomer pairs (I), (II) and (III). In addition, the product obtained has a chemical purity of over 98.5 wt. %, i.e. it contains less than 1 wt. % of impurities (see FIG. 3).

Analytics:

Gas chromatographic analysis of the first example revealed a composition corresponding to 96.894% by weight of enantiomeric pair (I), 0.577% by weight of enantiomeric pair (II) and 0.047% by weight of enantiomeric pair (III). In the second example, a composition corresponding to the following proportions was detected: 97.971% of enantiomeric pair (I), 0.979% of enantiomeric pair (II) and 0.072% of enantiomeric pair (III).

The corresponding values were determined by means of Thermo Fisher Scientific gas chromatographs (TRACE1300Series), using polyethylene glycol as column material.

Corresponding NMR measurements of the first example and a gas chromatographic analysis of the second example are shown in the figures.

NMR data of the first example:

H NMR: 7.38 m (1H), 7.25 m (2H), 7.21 m (1H), 5.46 d, J=6.60 (1H), 4.75 q, J=5.09 (1H), 3.32 dq, J=10.38, 6.13 (1H), 2.92 ddd, J=15.89, 6.52, 1.25 (1H), 2.49 d, J=16.00 (1H), 2.40 dt, J=10.44, 6.58 (1H), 1.35 d, J=5.11 (3H), 1.27 d, J=6.15 (3H).

Furthermore, the odorant mixture obtained has no measurable rotational value, so that it can be concluded that the enantiomers of the respective enantiomer pairs are each present in racemic form relative to one another, i.e. the enantiomer pairs (I), (II) and (III) are each racemic.

Comparative Example

While the isomers (I) and (II) are present in a ratio of at least 10:1 to each other, a comparative example shows that already the changes of the reflux ratio to 1:1 and of the head temperature to about 141° C. to 142° C. under otherwise identical distillation conditions lead to a quantitative ratio of the enantiomer pair (I) to the enantiomer pair (II) in the odorant mixture of only 1:2 to 2:1.

Consequently, by skillful choice of distillation conditions, it was possible to provide a diastereomer-enriched odorant mixture according to the invention, which exhibits the preferred and optimised floral fragrance.

Odour Description:

For the determination of the olfactory properties, the individual enantiomer pairs (I), (II) and (III) were obtained separately by chromatographic separation and evaluated with regard to their odour by a test panel of 8 test persons: The individual enantiomer pairs have the following odour profiles: The odour of enantiomer pair (I) can essentially be described as floral, rosy, transparent, radiant and smelling of geranium, while enantiomer pair (II) gives a floral, green, somewhat technical, grapefruit-smelling odour impression that is weaker compared to enantiomer pair (I). Enantiomer pair (III), on the other hand, has essentially a floral, technical, unclean and plastic-smelling odour profile.

The results of the olfactory properties test are shown in Table 1 below:

TABLE 1

| Fragrance description | Commercially available Magnolan | Isomer mixture according to claim 1 | Enantiomer pair 1 | Enantiomer pair 2 | Enantiomer pair 3 |
|---|---|---|---|---|---|
| Rose | 6 | 8 | 8 | 5 | 4 |
| Lily of the Valley | 6 | 5 | 6 | 7 | 3 |
| Orris/ Violet | 2 | 0 | 0 | 2 | 2 |
| Leafy vegetables | 5 | 2 | 2 | 6 | 5 |
| Jasmine/ Ylang | 3 | 2 | 2 | 3 | 2 |
| Orange blossom | 3 | 1 | 1 | 3 | 2 |
| Fruity | 5 | 3 | 2 | 6 | 5 |
| Indole-like | 3 | 0 | 0 | 2 | 5 |
| Plastic | 3 | 1 | 0 | 1 | 6 |

Table 1 shows that the enantiomer pair (III) and the commercially available magnolan produced in the comparative example have a strong plastic odour. In contrast, the mixture of isomers of the present invention according to claim 1 has a much lower plastic odour, as well as a more radiant rose note. Thus, the odour of the commercially available magnolan could be improved.

The odour of the overall racemic product, i.e. of the odorant mixture according to the invention, according to the examples according to the invention could be described in both cases as somewhat warmer, more intense and more naturally floral, rosy, transparent, radiant and smelling of geranium, while comparative odour mixtures with enantiomeric compositions deviating from the present description are characterised by the odour properties of enantiomer pairs (II) and/or (III) and consequently have a somewhat technical, grapefruit-smelling and weaker, i.e. less intense, impure and altogether less floral odour impression compared to enantiomer pair (I), which partly even shows intense technical or even reminiscent of plastic and impure notes. Therefore, the purified products according to the invention are preferable.

Commercially available Magnolan products, such as the Magnolan produced in the comparative example or the Magnolan raw product, also have a somewhat technical and plastic-smelling odour, which can thus be described as flowery, green, somewhat rosy, somewhat technical and smelling of grapefruit and plastic.

In contrast, the diastereomer-enriched odorant blends of the first and second aspects, as described herein, obtained from the process described herein, exhibit an exceedingly intensely radiant, balanced, natural, "clean" floral, rosy, transparent, somewhat warmer and geranium-scented odour, which is generally perceived as more pleasant, balanced and "clean" than the above-mentioned products, and has no technical or plastic-scented notes.

Accordingly, the process described herein demonstrated an efficient, simple and gentle distillative process for the effective and gentle distillative enrichment of the enantiomeric pair (I) and the provision of the diastereomerically enriched odorant mixture comprising the compounds of the general formula (A) according to the first and second aspects in high purity and yield. In particular, it was surprisingly possible to enrich the enantiomer pair (I) in a proportion of more than 95% by weight relative to the sum of the enantiomer pairs (I), (II) and (III) in the odorant mixture according to the invention and thus to effectively optimise the odour impression produced.

The invention claimed is:

1. A distillative process for the preparation of a diastereomer-enriched odorant mixture comprising compounds of the general formula (A):

Formula (A)

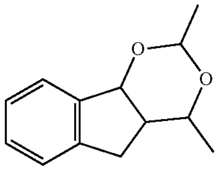

wherein the odorant mixture comprises the following mutually diastereomeric pairs of enantiomers:

Enantiomeric pair (I):

Formula (Ia)

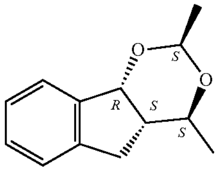

Formula (Ib)

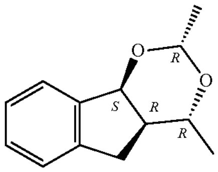

Enantiomeric pair (II):

-continued

Formula (IIa)

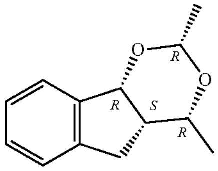

Formula (IIb)

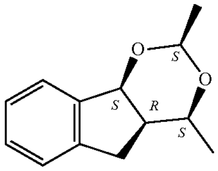

Enantiomeric pair (III):

Formula (IIIa)

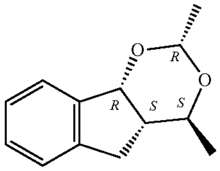

Formula (IIIb)

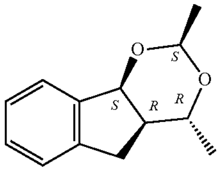

wherein the ratio of the enantiomeric pair (I) and the enantiomeric pair (II) to one another is at least 10:1;

wherein the ratio of the enantiomer pairs (I) and (III) to each other is at least 50:1; and wherein the process comprises the following distillation steps:

(a) separating by distillation a crude product comprising compounds of the general formula (A) in a first distillation step;

(b) subsequently fine distilling the crude product over one or more distillation steps to concentrate the enantiomeric pair (I) relative to the enantiomeric pairs (II) and (III), wherein the fine distillation comprises at least 15 separation steps.

2. The process according to claim 1, further comprising, before the distillative steps:

providing paraldehyde of formula (IV) or acetaldehyde;

Formula (IV)

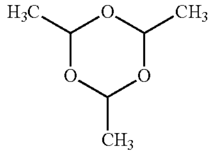

and reacting the paraldehyde or acetaldehyde with indene of the formula (V) under acid catalysis in a solvent, Formula (V)

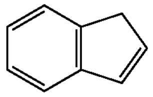

wherein the reaction of the paraldehyde or acetaldehyde with indene takes place at temperatures below 10° C.; and recovering the crude product comprising compounds of the general formula (A).

3. The process according to claim 1, wherein the fine distillation is carried out in a continuous process.

4. The process according to claim 1, wherein the fine distillation has a reflux ratio of at least 5:1.

5. The process according to claim 1, wherein the fine distillation is carried out at temperatures between 120° C. and 150° C.

6. The process according to claim 1, wherein the fine distillation is carried out at a reduced pressure of about 1 to 100 mbar.

7. The process according to claim 1, wherein the first distillation step is a thin film distillation.

8. The process according to claim 7, wherein the thin film distillation comprises two stages:

separating solvent at a reduced pressure of about 1 mbar to 400 mbar; and extracting the crude product comprising compounds of the general formula (A) at a reduced pressure of about 0 mbar to 100 mbar.

9. The process according to claim 7, wherein the first stage of thin film distillation is carried out at a sheath temperature of between 120° C. and 200° C. and wherein the second stage of thin film distillation is carried out at a sheath temperature of between 150° C. and 250° C.

10. A diastereomer-enriched odorant mixture comprising compounds of the general formula (A):

Formula (A)

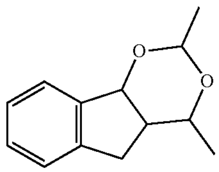

wherein the compounds of formula (A) comprise the following mutually diastereomeric enantiomer pairs of formulae (I), (II) and (III):

Enantiomeric pair (I):

Formula (Ia)

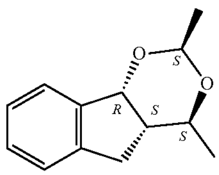

-continued

Formula (Ib)

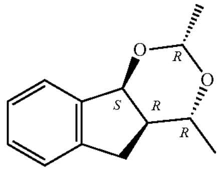

Enantiomeric pair (II):

Formula (IIa)

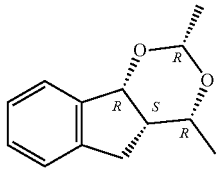

Formula (IIb)

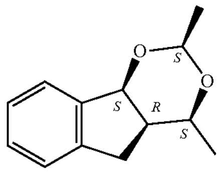

Enantiomeric pair (III):

Formula (IIIa)

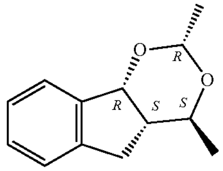

Formula (IIIb)

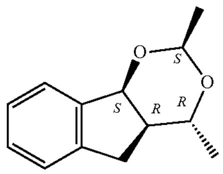

wherein the ratio of the enantiomeric pair (I) and the enantiomeric pair (II) to each other is at least 10:1; and wherein the ratio of the enantiomer pairs (I) and (III) to each other is at least 50:1.

11. The diastereomer-enriched odorant blend of claim 10, wherein the odorant blend comprises a total of at least 96.5% by weight of enantiomer pairs (I), (II) and (III).

12. A method of preparing an odorant composition comprising formulation the composition as a composition comprising the diastereomer-enriched odorant mixture according to claim 10.

13. An odorant composition comprising a sensory effective amount of the diastereomer-enriched odorant mixture according to claim 10.

14. A method of imparting, modifying, or enhancing a floral odour note in a perfumed product comprising formulating the perfumed product as a composition comprising a sensory effective amount of the diastereomer-enriched odorant composition according to claim 10.

15. A perfumed product comprising the diastereomer-enriched odorant mixture of claim 10.

16. The process according to claim 2, wherein the fine distillation is carried out in a continuous process.

17. The process according to claim 2, wherein the fine distillation has a reflux ratio of at least 5:1.

18. The process according to claim 2, wherein the fine distillation is carried out at temperatures between 120° C. and 150° C.

19. The process according to claim 2, wherein the fine distillation is carried out at a reduced pressure of about 1 to 100 mbar.

20. The process according to claim 2, wherein the first distillation step is a thin film distillation.

* * * * *